United States Patent [19]
Astle

[11] Patent Number: 5,882,597
[45] Date of Patent: Mar. 16, 1999

[54] BIOASSAY PLATE WASHER HAVING CONCENTRIC ASPIRATE AND WASH NEEDLES

[76] Inventor: Thomas W. Astle, 607 Harborview Rd., Orange, Conn. 06477

[21] Appl. No.: 935,133

[22] Filed: Sep. 22, 1997

[51] Int. Cl.[6] .............................. G01N 35/10; B08B 9/04
[52] U.S. Cl. .............................. 422/65; 422/63; 422/100; 436/49; 436/54; 134/170
[58] Field of Search .................. 422/63, 65, 81, 422/100, 103, 104; 436/43, 49, 54, 174, 180; 15/302, 304; 134/171, 170

[56] References Cited

U.S. PATENT DOCUMENTS

| | | | |
|---|---|---|---|
| 3,849,830 | 11/1974 | Wagner | 15/302 |
| 3,949,771 | 4/1976 | Dodge et al. | 134/94 |
| 4,053,284 | 10/1977 | Posch | 15/302 |
| 4,227,886 | 10/1980 | Bullock et al. | 422/64 |
| 4,559,664 | 12/1985 | Bohme et al. | 15/302 |
| 4,635,665 | 1/1987 | Namba et al. | 134/167 R |

*Primary Examiner*—Long V. Le
*Attorney, Agent, or Firm*—John H. Crozier

[57] ABSTRACT

In a preferred embodiment, a bioassay plate washer, including: a housing; a first wash assembly disposed in the housing; the first wash assembly including wash and aspirate manifolds having defined therein, respectively, a wash liquid chamber and a vacuum chamber; a plurality of wash needles for communication between the wash liquid chamber and a first point below the first wash assembly; a plurality of aspirate needles for communication between the vacuum chamber and a second point below the first point; and each one of the plurality of aspirate needles being disposed internally of each one of the wash needles.

6 Claims, 3 Drawing Sheets

5,882,597

BIOASSAY PLATE WASHER HAVING CONCENTRIC ASPIRATE AND WASH NEEDLES

BACKGROUND OF THE INVENTION

1. Field of the Invention

The present invention relates to the washing of bioassay plates generally and, more particularly, but not by way of limitation, to a novel washer for washing bioassay plates, the washer including concentric aspirate and wash needles.

2. Background Art

In clinical diagnostics and pharmaceutical research, a common protocol is enzyme linked immunosorbent assays (ELISA). In general terms, a reagent is bound to a container's surface. Other reagents react with the bound reagent, and are finally detected using an enzyme to cause a substrate to provide a color reaction. In these protocols, it is necessary to wash away the excess regent between each step.

The current de facto standard for ELISA protocols is to perform them in a 96-well microplate. Each well holds approximately 300 microliters. The wells are arranged on an 8×12 matrix on 9 mm centers. The antigen, or antibody, reagent is coated on the well surface. Typically, 200 microliters of a blocking reagent is added and allowed to react for a period of time with the antigen reagent. A plate washer is used to aspirate the blocking reagent from the well. Then, the well is refilled with a washing liquid and aspirated empty several times to remove any excess blocking reagent that is not bound to the side walls. This process is repeated several times with the other reagents used in the specific protocol.

Since the reaction is on the surface of the walls of the well and not in the liquid within the well, it is desirable to maximize the surface area and minimize the liquid reagents required to fill the well. This need for reduction in the use of reagents is driven by the cost of the reagents. Many antigens and antibodies must be grown in animals. This makes them precious.

To meet the demand for reduction in reagent use and cost and still meet the demands of high throughput screening, the trend is toward the use of a 384-well plate in the same overall physical dimensions as the current 96-well plate. The 384 wells are arranged in a 16×24 matrix on 4.5 mm center-to-center spacing. The brim volume of each well is approximately 80 microliters, with a working volume of around 30 microliters.

This close spacing obsoletes the plate washers that are currently on the market. The number of wells to be aspirated simultaneously increases four fold. This puts a different demand on the vacuum requirements for aspiration. The tight spacing requires a smaller, more precisely aligned wash and aspirate needle assembly.

For the foreseeable future, there will be a need to wash both 96-well and 384-well plates and to do so in a manner that washes all wells on a plate simultaneously. Heretofore, no plate washer has been known which could simultaneously wash all wells on a 384-well plate. Conventional washers for the latter type of plate employ two or three needles and treat one row of wells at a time.

Accordingly, it is a principal object of the present invention to provide a bioassay plate washer that can simultaneously wash all wells on a bioassay plate having a large number of wells.

It is a further object of the invention to provide such a bioassay plate washer that can easily accommodate bioassay plates having different numbers of wells.

It is an additional object of the invention to provide such a bioassay plate washer that is economically constructed.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a bioassay plate washer, comprising: a housing; a first wash assembly disposed in said housing; said first wash assembly including wash and aspirate manifolds having defined therein, respectively, a wash liquid chamber and a vacuum chamber; a plurality of wash needles for communication between said wash liquid chamber and a first point below said first wash assembly; a plurality of aspirate needles for communication between said vacuum chamber and a second point below said first point; and each one of said plurality of aspirate needles being disposed internally of each one of said wash needles.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Figure 1:
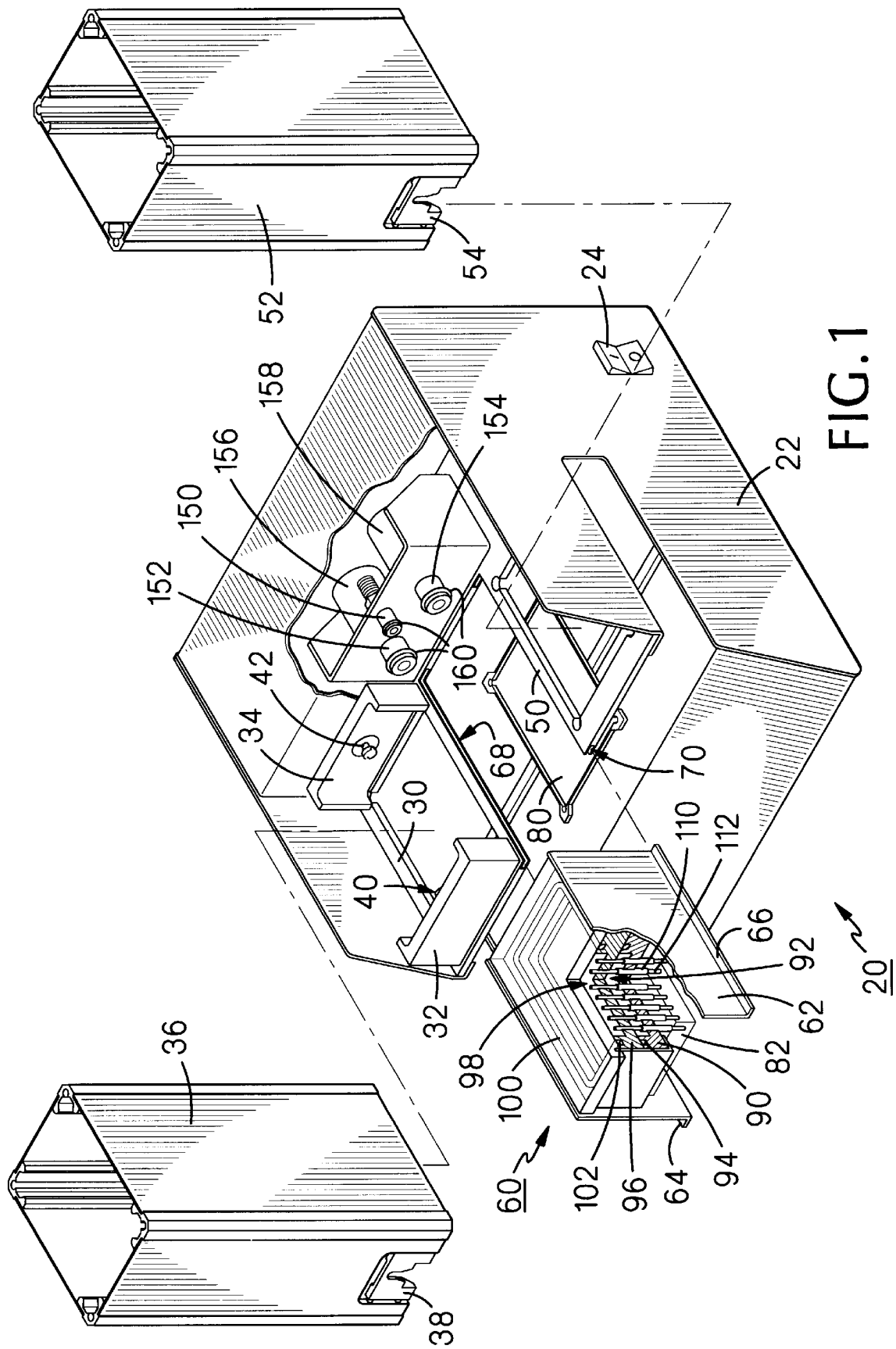
FIG. 1 is an isometric view, partially cutaway, of a plate washer according to the present invention.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

FIG. 1 illustrates a bioassay plate washer, generally indicated by the reference numeral 20, and constructed according to the present invention. Washer 20 includes a housing 22 and an on-off switch 24 connected to selectively activate or deactivate internal electrical/electronic control circuitry (not shown).

Housing 22 includes a horizontal, input cassette base support 30 with front and rear retaining supports 32 and 34, respectively, for supporting and retaining an input cassette 36. Input cassette 36 is arranged to hold therein in vertical alignment a plurality of bioassay trays (not shown) of the type described above, which bioassay trays may be of the 96-well or 384-well type, or they may have any other number of wells. Input cassette 36 includes at the base thereof an escapement mechanism 38 for the one-by-one downward dispensing of the bioassay trays. Escapement mechanism 38 is activated by solenoids 40 and 42 disposed, respectively, in front and rear retaining supports 32 and 34.

Similarly, a horizontal base support 50 is provided to support an output cassette 52 having an escapement mechanism 54 at the base thereof for receiving bioassay trays. It will be understood that front and rear retaining supports and solenoids for activating escapement mechanism 54 (none shown, for clarity) will be provided in connection with base support 50 and having the same function as the similar elements described above in connection with base support 30 and input cassette 36.

A wash head assembly, generally indicated by the reference numeral 60, includes a housing 62 having outwardly turned, parallel, horizontal flanges 64 and 66 formed at lower edges thereof for sliding insertion, respectively, into opposing, parallel, horizontally open channels 68 and 70 formed in the inner edges of base supports 30 and 50. When so inserted, wash head assembly 60 is removably frictionally secured in place and is accurately aligned with the other internal components of bioassay plate washer 20.

Disposed in housing 22 is a horizontal elevator plate 80 which is movable vertically and horizontally within the housing, as is described in detail below.

Figure 2:
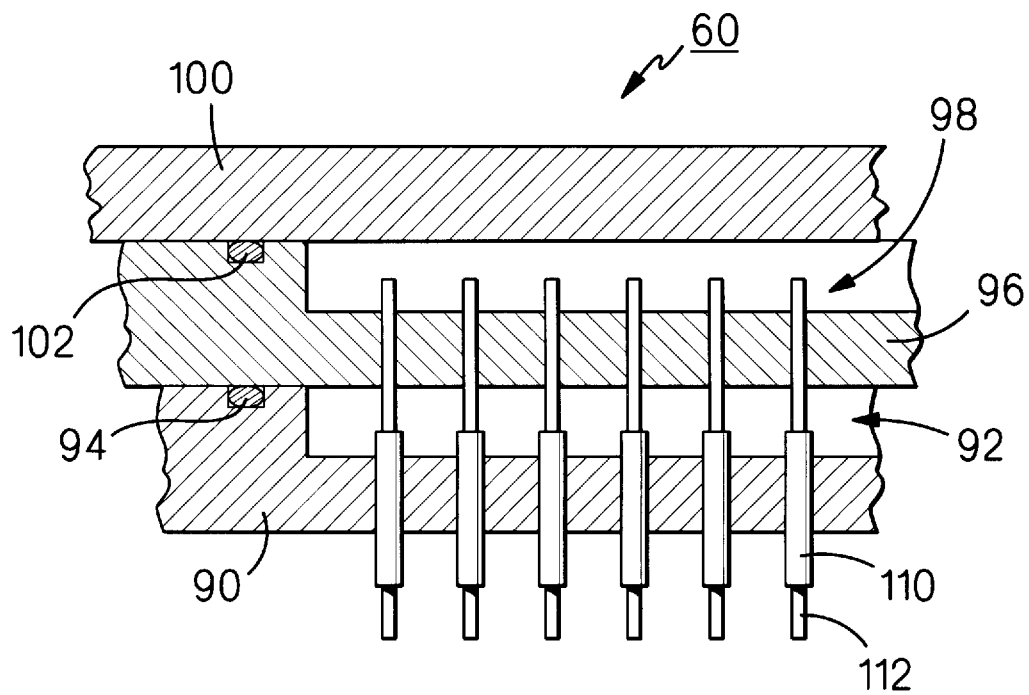
FIG. 2 is a fragmentary, side elevational, cross-sectional view of the needle arrangement of the plate washer.

Referring primarily now to FIG. 2, wash head assembly 60 includes a wash manifold 90 having defined therein a wash liquid chamber 92. Sealed to the upper surface of wash manifold 90 by a suitable sealing member 94, and forming an upper wall of the wash manifold, is an aspirate manifold 96 having defined therein a vacuum chamber 98. A cover 100 is sealed to the upper surface of aspirate manifold 96 by means of a suitable sealing member 102 and forms an upper wall of the aspirate manifold. A plurality of vertical wash needles, as at 110, are pressed into the lower portion of wash manifold and extend between wash liquid chamber 92 and a point below the wash manifold. A plurality of vertical aspirate needles, as at 112, are pressed into aspirate manifold 96 and extend concentrically through wash needles 110 between vacuum chamber 98 and a point below the lower termination of the wash needles. The lower terminations of wash needles 110 and aspirate needles 112 are arranged such that the needles may be inserted into a well on a bioassay plate (not shown), with the bottoms of the aspirate needles reaching to the bottoms of the wells on the plate.

Figure 3:
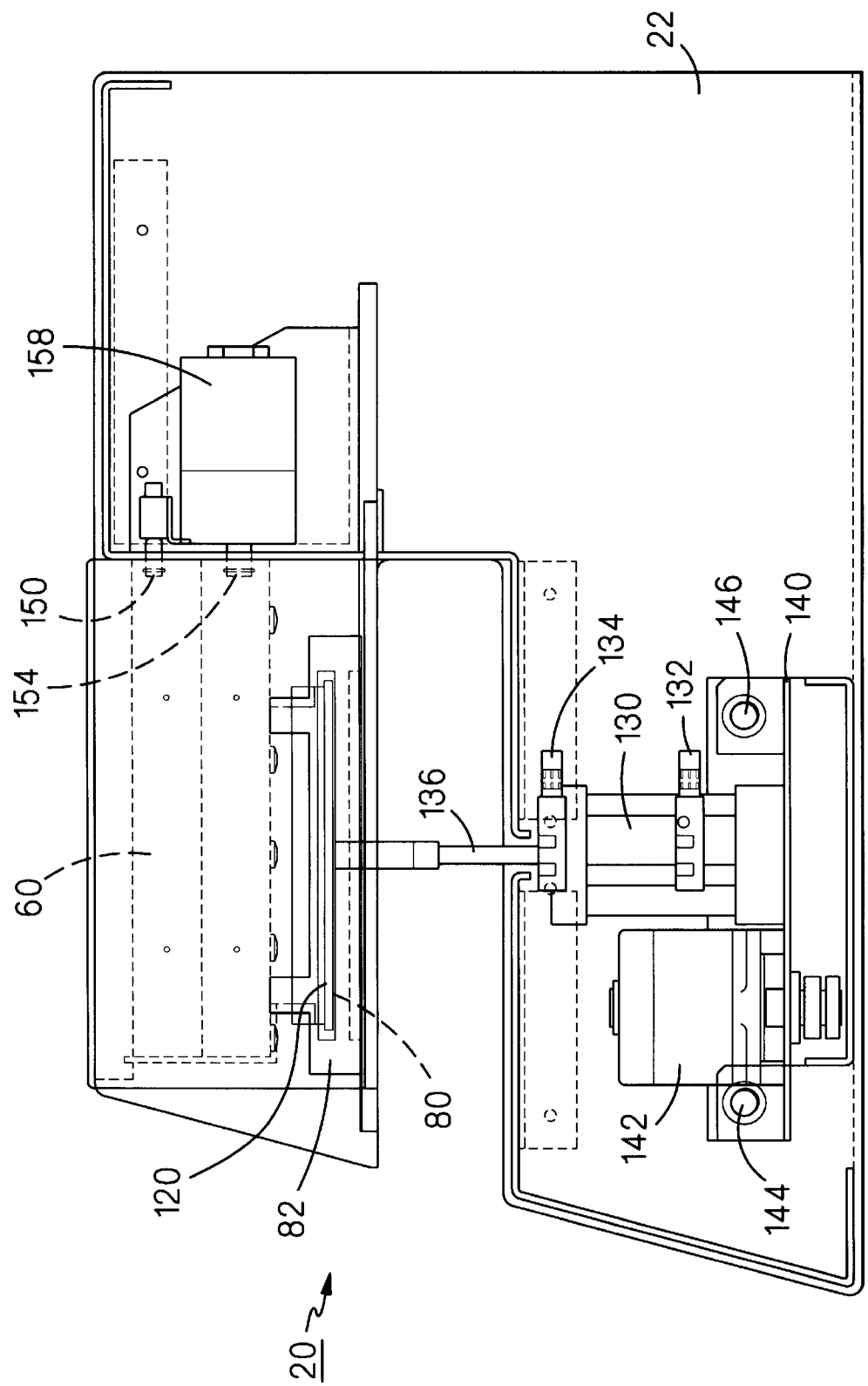
FIG. 3 is a side elevational view, in cross-section, of the plate washer.

FIG. 3 illustrates the mechanisms which cause vertical and horizontal movement of elevator plate 80, shown on FIG. 3 in its elevated position placing a bioassay tray 120 in operating engagement with wash head assembly 60. Elevator plate 80 is moved vertically up and down by means of a pneumatic cylinder 130 having inlet and exhaust ports 132 and 134, respectively (external tubing not shown), and a vertical piston 136 to the distal end of which elevator plate 80 is attached. A carriage 140 on which pneumatic cylinder 130 and a stepper motor 142 are mounted is selectively driven back and forth in housing 22 (FIG. 1) along horizontal parallel rails 144 and 146 by means of rotation of the stepper motor.

Wash head assembly 60 is arranged such that when the wash head assembly is inserted in bioassay plate washer 20, a vacuum connection 150 (FIG. 1) fixedly mounted in housing 22 operatively engages vacuum chamber 98 for the connection thereof to a vacuum source. Likewise, such insertion causes wash liquid connections 152 and 154 to operatively engage wash liquid chamber 92 for the connection thereof to one or more sources of wash liquid. The same wash liquid may be supplied through wash liquid connections 152 and 154 or different wash liquids may be so supplied. Solenoid valves 156 and 158 connected, respectively, to wash liquid connections 152 and 154 selectively open or close the connections. O-rings 160 provide sealing of vacuum connection 150 and wash liquid connections 152 and 154 to wash head assembly 60.

In operation, elevator plate 80 is moved by carriage 140 (FIG. 3) to a position underneath base support 30 and is raised by pneumatic cylinder 130 and piston 136 to the base support. Then, escapement mechanism 38 (FIG. 1) is operated to dispense one bioassay plate from input cassette 36 onto elevator plate 80. Next, elevator plate 80 is lowered, moved horizontally to underneath wash head assembly 60 and raised to the position shown on FIG. 3. In order to ensure that the bioassay plate is properly aligned with wash needles 110 and aspirate needles 112, a guide nest 82 is provided. Guide nest 82 is attached to and depends from the bottom of wash head assembly 60 and is permitted only vertical movement with respect thereto. Elevator plate 80 with bioassay plate 120 thereon rises through a close fitting, rectangular opening in guide nest 82 and is, thus, properly oriented. This is especially important when bioassay plate 120 has 384 wells, since aspirate needles 112 used therewith are especially small and fragile and would be easily damaged if there were any misalignment.

The conventional washing, soaking, and aspirating operations are then carried out. Finally, elevator plate 80 is lowered, moved to underneath output cassette 52 (FIG. 1) and raised. Escapement mechanism 54 is then activated to insert the bioassay plate in the bottom of output cassette 52. The procedure is repeated for each bioassay plate in input cassette 36. If one or more cycles are desired, elevator plate 80 can be operated to transfer the bioassay plates in output cassette 52 to input cassette 36.

All of the above operations are carried out in an automatic, programmed manner under control of the electrical/electronic circuitry in housing 22.

A plurality of conventional transmissive photodetectors are employed for sensing and verifying positions of the various moving elements of bioassay plate washer 20.

The concentric needle arrangement is compact and, since aspirate needles 112 pass inside of wash needles 110 through wash manifold 90 (FIG. 2), there is no need to seal the aspirate needles to the wash manifold. The needle arrangement of the present invention provides a wash unit that is compact enough that all wells on a 384-well bioassay plate can be washed simultaneously.

A further advantage of the present invention is that wash head assembly 60 can be easily removed and replaced with another wash head assembly. With no other changes to bioassay plate washer 20, the washer can be converted from use with a 96-well plate to use with a 384-well plate or vice versa. Similarly, plates with other numbers of wells can be accommodated as well.

A potential problem presented by the close clearance between a wash needle 110 and an aspirate needle 112 is that the aspirate needle may touch the inner diameter of the wash needle. Ordinarily, an annular liquid seal is formed between the inner diameter of wash needle 110 and the outer diameter of the aspirate needle 112, due to surface tension an and the fact that no air can enter wash liquid chamber 92. However, when aspirate needle 112 touches the inner diameter of wash needle 110, the seal is broken and liquid can run down the enlarged space created and air can rise through the narrow space created. With air entering wash liquid chamber 92, all wash needles 110 begin leaking liquid.

Figure 4:
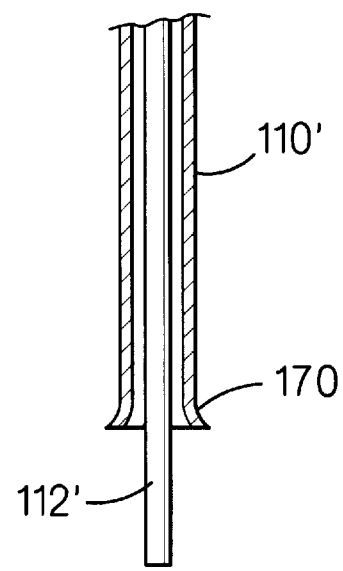
FIG. 4 is an enlarged, fragmentary, side elevational view of an alternative needle arrangement.

A solution to this potential problem is shown on FIG. 4 where a downwardly open flare 170 is provided at the distal end of a wash needle 110'. Now when an aspirate needle 112' disposed in wash needle 110' touches the inner diameter of the wash needle, a somewhat distorted, but still intact, annular liquid seal will remain in the flared portion of the wash needle.

A further solution to this potential problem is to coat the outside of aspirate needle 112' with teflon so as to make that surface hydrophobic such that it does not attract liquid.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. A bioassay plate washer, comprising:
   (a) a housing;
   (b) a first wash assembly disposed in said housing;
   (c) said first wash assembly including wash and aspirate manifolds having defined therein, respectively, a wash liquid chamber and a vacuum chamber;
   (d) a plurality of wash needles for communication between said wash liquid chamber and a first point below said first wash assembly;
   (e) a plurality of aspirate needles for communication between said vacuum chamber and a second point below said first point;
   (f) each one said plurality of aspirate needles being disposed internally of each one of said wash needles; and
   (g) distal ends of said plurality of wash needles at said first point are downwardly flared.

2. A bioassay plate washer, as defined in claim 1, further comprising: means to automatically transport bioassay plates one by one into a washing relationship with said first wash assembly, with a one of said plurality of wash needles and a one of said plurality of aspirate needles inserted into each well defined in said bioassay plate.

3. A bioassay plate washer, as defined in claim 2, wherein: said means to automatically transport receives said bioassay plates from an input cassette, moves said bioassay plates one by one into said washing relationship with said first wash assembly, and then moves said bioassay plates one by one to an output cassette.

4. A bioassay plate washer, as defined in claim 3, wherein: said means to automatically transport transfers said bioassay plates one by one from said output cassette to said input cassette.

5. A bioassay plate washer, as defined in claim 1, wherein:
   (a) said first wash assembly is removably inserted in said housing;
   (b) when said first wash assembly is inserted in said housing, insertion thereof effects connection of said vacuum chamber to a vacuum source and connection of said wash liquid chamber to a wash liquid source; and
   (c) said first wash assembly is removable and replaceable with a second wash assembly having a needle matrix different from that of said first wash assembly, insertion of said second wash assembly effecting connection of a vacuum chamber defined therein to said vacuum source and connection of a wash liquid chamber defined therein to said wash liquid source.

6. A bioassay plate washer, comprising:
   (a) a housing;
   (b) a first wash assembly disposed in said housing, said wash assembly including a plurality of wash needles and a plurality of aspirate needles disposed therein in a first matrix;
   (c) means to transport a bioassay plate into washing relationship with said wash assembly; and
   (d) said first wash assembly being removable from said housing and replaceable with a second wash assembly having a plurality of wash needles and a plurality of aspirate needles disposed therein in a second matrix, wherein said second matrix being different from said first matrix.

* * * * *